United States Patent
Littrup et al.

(10) Patent No.: US 7,921,657 B2
(45) Date of Patent: *Apr. 12, 2011

(54) METHODS AND SYSTEMS FOR CRYOGENIC COOLING

(75) Inventors: Peter J. Littrup, Bloomfield Hills, MI (US); Alexei V. Babkin, Albuquerque, NM (US); Robert Duncan, Tijeras, NM (US); Sergey Boldarev, Moscow (RU)

(73) Assignee: Endocare, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/846,226

(22) Filed: Aug. 28, 2007

(65) Prior Publication Data

US 2008/0173028 A1  Jul. 24, 2008

Related U.S. Application Data

(60) Division of application No. 10/952,531, filed on Sep. 27, 2004, now Pat. No. 7,273,479, which is a continuation-in-part of application No. 10/757,768, filed on Jan. 14, 2004, now Pat. No. 7,410,484, said application No. 10/952,531 is a continuation-in-part of application No. 10/757,769, filed on Jan. 14, 2004, now Pat. No. 7,083,612.

(60) Provisional application No. 60/440,541, filed on Jan. 15, 2003, provisional application No. 60/440,662, filed on Jan. 15, 2003.

(51) Int. Cl.
F25D 17/02 (2006.01)

(52) U.S. Cl. .......................................... 62/64; 62/259.2

(58) Field of Classification Search .................. 62/51.1, 62/50.2, 50.4, 175, 259.2, 335, 383, 64; 606/20, 606/21, 22, 23, 24, 25, 26; 128/898
See application file for complete search history.

(56) References Cited

U.S. PATENT DOCUMENTS

| 3,062,017 | A | 11/1962 | Balcar |
| 3,942,010 | A | 3/1976 | Peterson |
| 3,993,123 | A | 11/1976 | Chu |
| 4,034,251 | A | 7/1977 | Haas |
| 4,167,771 | A | 9/1979 | Simons |
| 4,226,281 | A | 10/1980 | Chu |

(Continued)

FOREIGN PATENT DOCUMENTS

GB       1422535        1/1976

(Continued)

OTHER PUBLICATIONS

"Introduction to Process Engineering and Design" Chemical Engineering Series, S.B. Thakore and B.I. Bhatt, McGraw-Hill, 2008, pp. 27-28.

(Continued)

*Primary Examiner* — Mohammad M Ali
(74) *Attorney, Agent, or Firm* — Lawrence N. Ginsberg

(57) ABSTRACT

Methods and systems are provided for cooling an object with a cryogen having a critical point defined by a critical-point pressure and a critical-point temperature. A pressure of the cryogen is raised above a pressure value determined to provide the cryogen at a reduced molar volume that prevents vapor lock. Thereafter, the cryogen is placed in thermal communication with the object to increase a temperature of the cryogen along a thermodynamic path that maintains the pressure greater than the critical-point pressure for a duration that the cryogen and object are in thermal communication.

13 Claims, 8 Drawing Sheets

U.S. PATENT DOCUMENTS

| | | | |
|---|---|---|---|
| 4,281,268 A | 7/1981 | Sawa | |
| 4,384,360 A | 5/1983 | Kitadate | |
| 4,418,421 A | 11/1983 | Kitadate | |
| 4,519,389 A | 5/1985 | Gudkin | |
| 4,548,045 A | 10/1985 | Altares et al. | 62/63 |
| 4,802,475 A | 2/1989 | Weshahy | |
| 4,838,041 A | 6/1989 | Bellows | |
| 4,843,446 A | 6/1989 | Nishino | |
| 4,945,562 A | 7/1990 | Staub | |
| 4,946,460 A | 8/1990 | Merry | |
| 4,982,080 A | 1/1991 | Wilson | |
| 5,012,505 A | 4/1991 | Zupancic | |
| 5,155,093 A | 10/1992 | Den | |
| 5,173,606 A | 12/1992 | Weinberger | |
| 5,212,626 A | 5/1993 | Bell | |
| 5,214,925 A * | 6/1993 | Hoy et al. | 62/50.6 |
| 5,254,116 A | 10/1993 | Baust | |
| 5,274,237 A | 12/1993 | Gallagher | |
| 5,275,595 A | 1/1994 | Dobak, III | |
| 5,334,181 A | 8/1994 | Rubinsky | |
| 5,405,533 A | 4/1995 | Hazlebeck | |
| 5,433,717 A | 7/1995 | Rubinsky | |
| 5,471,844 A | 12/1995 | Levi | |
| 5,494,039 A | 2/1996 | Onik | |
| 5,504,924 A | 4/1996 | Ohashi | |
| 5,520,682 A | 5/1996 | Baust | |
| 5,531,742 A | 7/1996 | Barken | |
| 5,661,980 A * | 9/1997 | Gallivan | 62/51.1 |
| 5,741,248 A | 4/1998 | Stern | |
| 5,757,885 A | 5/1998 | Yao | |
| 5,800,487 A | 9/1998 | Mikus | |
| 5,800,488 A | 9/1998 | Crockett | |
| 5,816,052 A | 10/1998 | Foote | |
| 5,899,897 A | 5/1999 | Rabin | |
| 5,901,783 A | 5/1999 | Dobak, III | |
| 5,910,104 A | 6/1999 | Dobak, III | |
| 5,916,212 A | 6/1999 | Baust et al. | 606/22 |
| 5,950,444 A | 9/1999 | Matsunaga | |
| 5,978,697 A | 11/1999 | Ma Ytal | |
| 5,993,444 A | 11/1999 | Ammar | |
| 5,997,781 A * | 12/1999 | Nishikawa et al. | 264/45.1 |
| 6,039,730 A | 3/2000 | Rabin | |
| 6,074,412 A | 6/2000 | Mikus | |
| 6,139,544 A | 10/2000 | Mikus | |
| 6,142,991 A | 11/2000 | Schatzberger | |
| 6,179,831 B1 | 1/2001 | Bliweis | |
| 6,190,378 B1 | 2/2001 | Jarvinen | |
| 6,193,644 B1 | 2/2001 | Dobak, III | |
| 6,235,018 B1 | 5/2001 | LePivert | |
| 6,237,355 B1 | 5/2001 | Li | 62/293 |
| 6,251,105 B1 | 6/2001 | Mikus | |
| 6,263,046 B1 | 7/2001 | Rogers | |
| 6,307,916 B1 | 10/2001 | Rogers | |
| 6,341,629 B1 * | 1/2002 | Clark et al. | 141/83 |
| 6,377,659 B1 | 4/2002 | Snyder | |
| 6,396,901 B1 | 5/2002 | Hell | |
| 6,451,011 B2 | 9/2002 | Tu | |
| 6,471,694 B1 | 10/2002 | Kudaravalli | |
| 6,475,212 B2 | 11/2002 | Dobak, III | |
| 6,477,231 B2 | 11/2002 | Snyder | |
| 6,486,078 B1 * | 11/2002 | Rangarajan et al. | 438/778 |
| 6,527,765 B2 | 3/2003 | Kelman et al. | 606/22 |
| 6,530,420 B1 | 3/2003 | Takada | |
| 6,544,176 B2 | 4/2003 | Mikus | |
| 6,584,332 B2 | 6/2003 | Yoshitake | |
| 6,602,276 B2 | 8/2003 | Dobak, III | |
| 6,622,494 B1 | 9/2003 | Pourrahimi | |
| 6,622,507 B2 | 9/2003 | Cotte | |
| 6,628,002 B2 | 9/2003 | Ritz | |
| 6,648,879 B2 | 11/2003 | Joye et al. | |
| 6,706,037 B2 | 3/2004 | Zvuloni et al. | 606/21 |
| 6,737,225 B2 * | 5/2004 | Miller | 430/329 |
| 6,812,464 B1 | 11/2004 | Sobolewski | |
| 6,848,458 B1 * | 2/2005 | Shrinivasan et al. | 134/108 |
| 2001/0024485 A1 | 9/2001 | Rogers | |
| 2002/0040220 A1 | 4/2002 | Zvuloni | |
| 2002/0062831 A1 | 5/2002 | Beyar | |
| 2002/0087152 A1 | 7/2002 | Mikus | |
| 2002/0151331 A1 | 10/2002 | Abdelmonem | |
| 2004/0027462 A1 | 2/2004 | Hing | |
| 2004/0112067 A1 | 6/2004 | Bishop | |
| 2004/0118144 A1 | 6/2004 | Hsu | |
| 2004/0163797 A1 | 8/2004 | Cosley | |
| 2004/0218725 A1 | 11/2004 | Radley | |

FOREIGN PATENT DOCUMENTS

WO  WO/02/096270 A2  12/2002

OTHER PUBLICATIONS

"CRC Handbook of Thermophysical and Thermochemical Data", D.R. Lide and H.V. Kehiaian, CRC Press, 1994, p. 375.

Supplementary European Search Report Regarding Application No. EP05858178.6 Dated Nov. 5, 2010.

* cited by examiner

METHODS AND SYSTEMS FOR CRYOGENIC COOLING

CROSS-REFERENCES TO RELATED APPLICATIONS

This application is a Division of U.S. patent application Ser. No. 10/952,531 entitled METHODS AND SYSTEMS FOR CRYOGENIC COOLING which is a continuation-in-part of U.S. patent application Ser. No. 10/757,769, (U.S. Pat. No. 7,083,612 issued Aug. 1, 2006) entitled "CRYOTHERAPY SYSTEM," filed Jan. 14, 2004 by Peter J. Littrup et al., which is a nonprovisional claiming the benefit of the filing date of U.S. Prov. Appl. No. 60/440,662, entitled "CRYOSURGICAL SYSTEM," filed Jan. 15, 2003 by Peter Littrup et al. This application is also a continuation-in-part of U.S. patent application Ser. No. 10/757,768, entitled "CRYOTHERAPY PROBE," filed Jan. 14, 2004 by Peter J. Littrup et al., which is a nonprovisional claiming the benefit of the filing date of U.S. Prov. Pat. Appl. No. 60/440,541, entitled "CRYOSURGICAL PROBE," filed Jan. 15, 2003 by Peter Littrup et al. The entire disclosures U.S. patent application Ser. No. 10/952,531; U.S. patent application Ser. No. 10/757,769, U.S. Pat. No. 7,083,612; U.S. patent application Ser. No. 10/757,768; U.S. Prov. Appl. No. 60/440,662; and U.S. Prov. Pat. Appl. No. 60/440,541 are incorporated herein by reference for all purposes, including the appendices.

BACKGROUND OF THE INVENTION

This application relates to methods and systems for cryogenic cooling. "Cryogenic cooling" refers generally to processes that use liquefied gases, i.e. "cryogens," in providing the cooling, which may take the form of freezing or simply chilling a system or material.

There are numerous applications, both medical and nonmedical, in which it is desirable to provide effective cooling. Any cooling process may be considered as involving one or more of four basic processes that result in removal of a heat load: evaporation, conduction, radiation, and convection. One challenge that is presented in cryogenic cooling techniques results from the process of evaporation, and may be understood by considering cooling within a small channel. The process of evaporation of a liquefied gas results in enormous expansion as the liquid converts to a gas; the volume expansion is on the order of a factor of 200. In a small-diameter system, this degree of expansion consistently results in a phenomenon known in the art as "vapor lock." The phenomenon is exemplified by the flow of a cryogen in a thin-diameter tube, such as is commonly provided in a cryoprobe. A relatively massive volume of expanding gas that forms ahead of it impedes the flow of the liquid cryogen. Traditional techniques that have been used to avoid vapor lock have included restrictions on the diameter of the tube, requiring that it be sufficiently large to accommodate the evaporative effects that lead to vapor lock. Other complex cryoprobe and tubing configurations have been used to "vent" $N_2$ gas as it formed along transport tubing. These designs also contributed to limiting the cost efficacy and probe diameter.

There is accordingly a general need in the art for improved methods and systems for providing cryogenic cooling.

BRIEF SUMMARY OF THE INVENTION

Embodiments of the invention thus provide methods and systems for cooling an object. The methods and systems provide changes in pressure/temperature characteristics that avoid the occurrence of vapor lock by following a thermodynamic path that never crosses a liquid-gas phase line of the cryogen. In a number of embodiments, this is achieved by keeping the pressure of the cryogen near or above its critical-point pressure. In many embodiments, the cryogen comprises nitrogen ($N_2$), although other cryogens may be used in other embodiments.

In a first set of embodiments, a method is provided for cooling an object with a cryogen having a critical point defined by a critical-point pressure and a critical-point temperature. A pressure of the cryogen is raised above its critical-point pressure. Thereafter, the cryogen is placed n thermal communication with the object to increase a temperature of the cryogen along a thermodynamic path that maintains the pressure greater than the critical-point pressure for a duration that the cryogen and object are in thermal communication.

In some instances, the thermodynamic path may increase the temperature of the cryogen to an ambient temperature. The pressure of the cryogen may be reduced to an ambient pressure after removing the cryogen from thermal communication with the object. In some embodiments, after raising the pressure of the cryogen above its critical-point temperature and prior to placing the cryogen in thermal communication with the object, the temperature of the cryogen is reduced without decreasing the pressure of the cryogen below its critical-point pressure. For example, the temperature of the cryogen may be reduced by placing the cryogen in thermal communication with a second liquid cryogen having a temperature lower than the temperature of the cryogen. The cryogen and second cryogen may be chemically identical, and the second liquid cryogen may be substantially at ambient pressure. In one embodiment, the pressure of the cryogen is substantially constant while reducing the temperature of the cryogen.

When the pressure of the cryogen is raised above its critical-point pressure, the pressure of the cryogen may be raised to near or approximately at its critical-point pressure. Also, when the pressure of the cryogen is raised above its critical-point pressure, the cryogen may be provided at approximately its critical-point temperature. In one embodiment, the cryogen is provided at a temperature within ±10% of its critical-point temperature. The pressure of the cryogen may be raised above its critical-point pressure in one embodiment by placing the cryogen within a thermally insulated tank and applying heat within the tank at least until a predetermined pressure within the tank is reached.

In a second set of embodiments, another method is provided for cooling an object with a cryogen having a critical point defined by a critical-point pressure and a critical-point temperature. A pressure of the cryogen is raised to between 0.8 and 1.2 of its critical point pressure and the cryogen is provided at a temperature within ±10% of its critical-point temperature. The temperature of the cryogen is thereafter reduced without decreasing the pressure below 0.8 times its critical-point pressure. Thereafter, the cryogen is placed in thermal communication with the object to increase the temperature of the cryogen to an ambient temperature along a thermodynamic path that maintains a pressure greater than 0.8 times the critical-point pressure for a duration that the cryogen and object are in thermal communication. The cryogen is subsequently removed from thermal communication with the object and the pressure of the cryogen is reduced to an ambient pressure.

In a third set of embodiments, a further method is provided for cooling an object with a cryogen having a critical point defined by a critical-point pressure and a critical-point temperature. A pressure of the cryogen is raised to near its critical-point pressure. Thereafter, the cryogen is placed in thermal communication with the object to increase a temperature of the cryogen along a thermodynamic path that maintains the pressure near the critical-point pressure for a duration that the cryogen and object are in thermal communication. The pressure may be raised to near the critical-point pressure by raising the pressure of the cryogen to greater than a pressure value determined to provide the cryogen at a reduced molar volume that prevents vapor lock, with the thermodynamic path maintaining the pressure above the determined pressure value. In some instances, the determined pressure value is between 0.8 and 1.2 times the critical-point pressure.

In a fourth set of embodiments, a system is provided for cooling an object with a cryogen having a critical point defined by a critical-point pressure and a critical-point temperature. A cryogen generator is adapted to increase a pressure of the cryogen. A valve is provided at an outlet of the cryogen generator and adapted to release a flow of the cryogen when the pressure of the cryogen exceeds a predetermined pressure within the cryogen generator. The predetermined pressure is greater than a pressure value determined to provide the cryogen at a reduced molar volume that prevents vapor lock. A cryogenic application device is also provided and adapted to be brought into thermal communication with the object. A conduit connects the valve with the cryogenic application device for transporting the cryogen from the valve to the cryogenic application device. A flow controller regulates flow of cryogen through the conduit and cryogenic application device. The cryogen increases in temperature when the application device is in thermal communication with the object along a thermodynamic path that maintains the pressure of the cryogen above the predetermined pressure for a duration that the application device and cryogen are in thermal communication.

The cryogen generator may comprise a thermally insulated tank having an interior volume for holding the cryogen and a heating element for applying heat within the interior volume. In one embodiment, the heating element comprises a resistive heating element. A bath of a second liquid cryogen may surround a portion of the conduit between the valve and the cryogenic application device. In one embodiment, the bath of the second liquid cryogen is at substantially ambient pressure. In another embodiment, the cryogen and second cryogen are chemically identical.

In certain embodiments, the cryogen generator comprises a plurality of cryogen generators and the valve comprises a plurality of valves. Each of the plurality of cryogen generators is adapted to increase the pressure of the cryogen. Each of the plurality of valves is provided at an outlet of one of the plurality of cryogen generators and configured to release a flow of the cryogen when the pressure of the cryogen exceeds a predetermined pressure within the one of the plurality of cryogen generators. The conduit is configured to provide a selective connection between one of the plurality of valves and the cryogenic application device. In some such embodiments, the system further comprises a liquid bath of the cryogen, with the plurality of cryogen generators disposed within the liquid bath. In addition, the system may further comprise a plurality of heat exchangers, each of which is disposed within the liquid bath of the cryogen and in fluid communication between a respective one of the plurality of cryogen generators and the conduit. Each of the plurality of cryogen generators may additionally comprise an inlet to receive cryogen from the liquid bath of the cryogen. The cryogenic application device may comprise a detachable spray control nozzle, which in some instances may comprise a vent adapted to release cryogen reflected during use of the cryogenic application device. In one embodiment, the system further comprises a thermometry device adapted to measure a temperature of the object.

In a fifth set of embodiments, a method is provided for cooling an object with a cryogen having a critical point defined by a critical-point pressure and a critical-point temperature. A pressure of the cryogen is raised in a first cryogen generator above a pressure value determined to provide the cryogen at a reduced molar volume that prevents vapor lock. Thereafter, the cryogen is flowed from the first cryogen generator to be in thermal communication with the object and to have a pressure greater than the critical-point pressure while the cryogen and object are in thermal communication. Thereafter, a pressure of the cryogen in a second cryogen generator is raised above the determined pressure value. Thereafter, the cryogen from the second cryogen generator is flowed to be in thermal communication with the object and to have a pressure greater than the determined pressure value while the cryogen and object are in thermal communication. Thereafter, cryogen in the first cryogen generator is replenished.

In some such embodiments, when cryogen is flowed from the first or second cryogen generator, it is flowed through a conduit in thermal communication with a liquid bath to reduce a temperature of the cryogen. In one embodiment, the cryogen and liquid cryogen bath are chemically identical, with cryogen in the first cryogen generator being replenished from the liquid cryogen bath. When the pressure of the cryogen is raised above the determined pressure value in the first and second cryogen generators, it may be raised to near its critical-point pressure. In one embodiment, applying heat within a thermally insulated tank at least until a predetermined pressure within the thermally insulated tank is reached raises the pressure.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sub-label is associated with a reference numeral and follows a hyphen to denote one of multiple similar components. When reference is made to a reference numeral without specification to an existing sub-label, it is intended to refer to all such multiple similar components.

DETAILED DESCRIPTION OF THE INVENTION

Embodiments of the invention make use of thermodynamic processes using cryogens that provide cooling without encountering the phenomenon of vapor lock. Various other benefits and advantages provided in different embodiments of the invention are apparent from the following description.

Figure 1A:
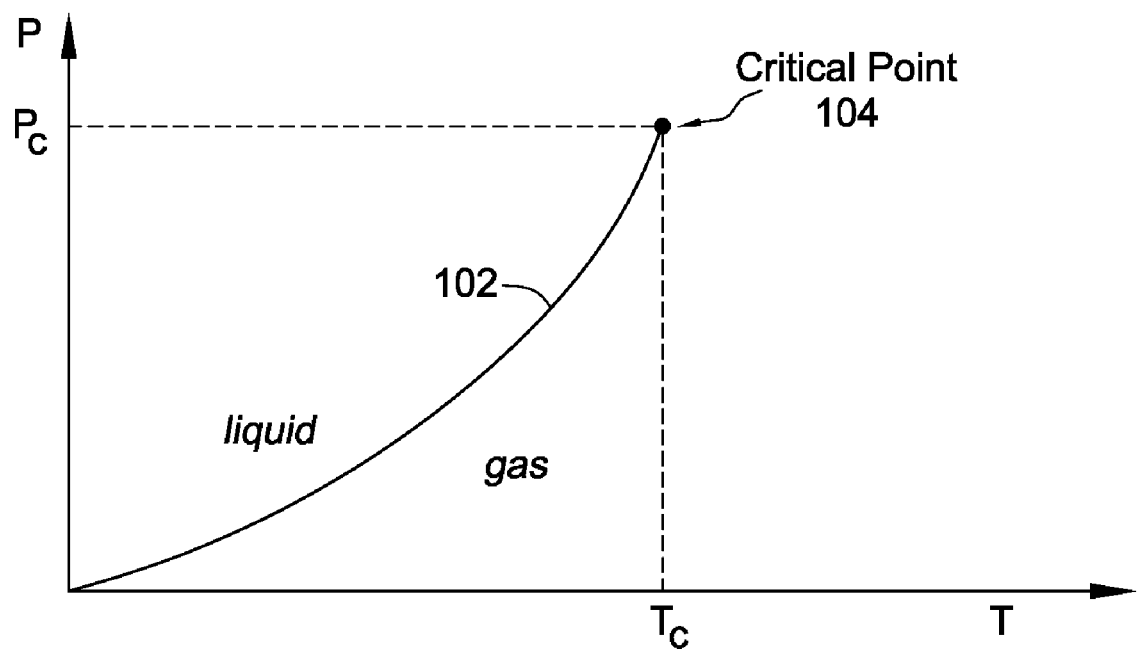
FIG. 1A illustrates a typical cryogen phase diagram.

This application uses phase diagrams to illustrate and compare various thermodynamic processes. Such phase diagrams are well known in the art and an example typical for a cryogen is provided in FIG. 1A. The axes of the diagram correspond to pressure P and temperature T, and includes a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen $N_2$, the critical point is at $P_c$=33.94 bar and $T_c$= −147.15° C.

When a fluid has both liquid and gas phases present during a gradual increase in pressure, the system moves up along the liquid-gas phase line 102. In the case of $N_2$, the liquid at low pressures is up to two hundred times more dense than the gas phase. A continual increase in pressure causes the density of the liquid to decrease and the density of the gas phase to increase, until they are exactly equal only at the critical point 104. The distinction between liquid and gas disappears at the critical point 104. The blockage of forward flow by gas expanding ahead of the liquid cryogen is thus avoided by conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryoprobe tip.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase. All gases obey quite well the following van der Waals equation of state:

$$\left(p + \frac{3}{v^2}\right)(3v - 1) = 8t,\quad\text{[Eq. 1]}$$

where $p \equiv P/P_c$, $v \equiv V/V_c$, and $t \equiv T/T_c$, and $P_c$, $V_c$, and $T_c$ are the critical pressure, critical molar volume, and the critical temperature respectively. The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley, *Introduction to Phase Transitions and Critical Phenomena* (Oxford Science Publications, 1971), the entire disclosure of which is incorporated herein by reference for all purposes. Rearranging Eq. 1 provides the following expression for v as a function of p and t:

$$pv^3 - (p+8t)v^2 + 9v - 3 = 0. \quad\text{[Eq. 2]}$$

The reduced molar volume of the fluid v may thus be thought of as being an exact function of only the reduced pressure t and the reduced pressure p.

Typically, in embodiments of the invention, the reduced pressure p is fixed at a constant value of approximately one, and hence at a fixed physical pressure near the critical pressure, while the reduced temperature t varies with the heat load applied to the needle. If the reduced pressure p is a constant set by the engineering of the system, then the reduced molar volume v is an exact function of the reduced temperature t. In embodiments of the invention, the needle's operating pressure p may be adjusted so that over the course of variations in the temperature t of the needle, v is maintained below some maximum value at which the vapor lock condition will result. It is generally desirable to maintain p at the lowest value at which this is true since boosting the pressure to achieve higher values of p may involve use of a more complex and more expensive compressor, resulting in more expensive procurement and maintenance of the entire needle support system and lower overall wall plug efficiency. As used herein, "wall plug efficiency" refers to the total cooling power of a needle divided by the power obtained from a line to operate the system.

The conditions that need to be placed on v depend in a complex and non-analytic way on the volume flow rate dV/dt, the heat capacity of the liquid and vapor phases, and the transport properties such as the thermal conductivity, viscosity, etc., in both the liquid and the vapor. This exact relationship cannot be derived in closed form algebraically, but may be determined numerically by integrating the model equations that describe mass and heat transport within the needle. Conceptually, vapor lock occurs when the rate of heating of the needle produces the vapor phase, and when the cooling power of this vapor phase, which is proportional to the flow rate of the vapor times its heat capacity divided by its molar volume, is not able to keep up with the rate of heating to the needle. When this occurs, more and more of the vapor phase is formed in order to absorb the excess heat through the conversion of the liquid phase to vapor in the cryogen flow. This creates a runaway condition where the liquid converts into vapor phase to fill the needle, and effectively all cryogen flow stops due to the large pressure that results in this vapor phase as the heat flow into the needle increases its temperature and pressure rapidly. This condition is called "vapor lock." Since the liquid and vapor phases are identical in their molar volume, and hence cooling power at the critical point, the cooling system at or above the critical point can never vapor lock. But for conditions slightly below the critical below the critical point, the needle may avoid vapor lock as well. A relationship between a minimum acceptable molar volume, corresponding to the minimum acceptable gas phase density, and dimensions of the needle, flow rate, and thermophysical properties of gas and liquid phases is a consequence of a manifestly complex nonlinear system. A determination of how large v may be, and hence how small p may be, to reliably avoid vapor lock may be determined experimentally, as illustrated with the data shown in FIG. 1B.

Figure 1B:
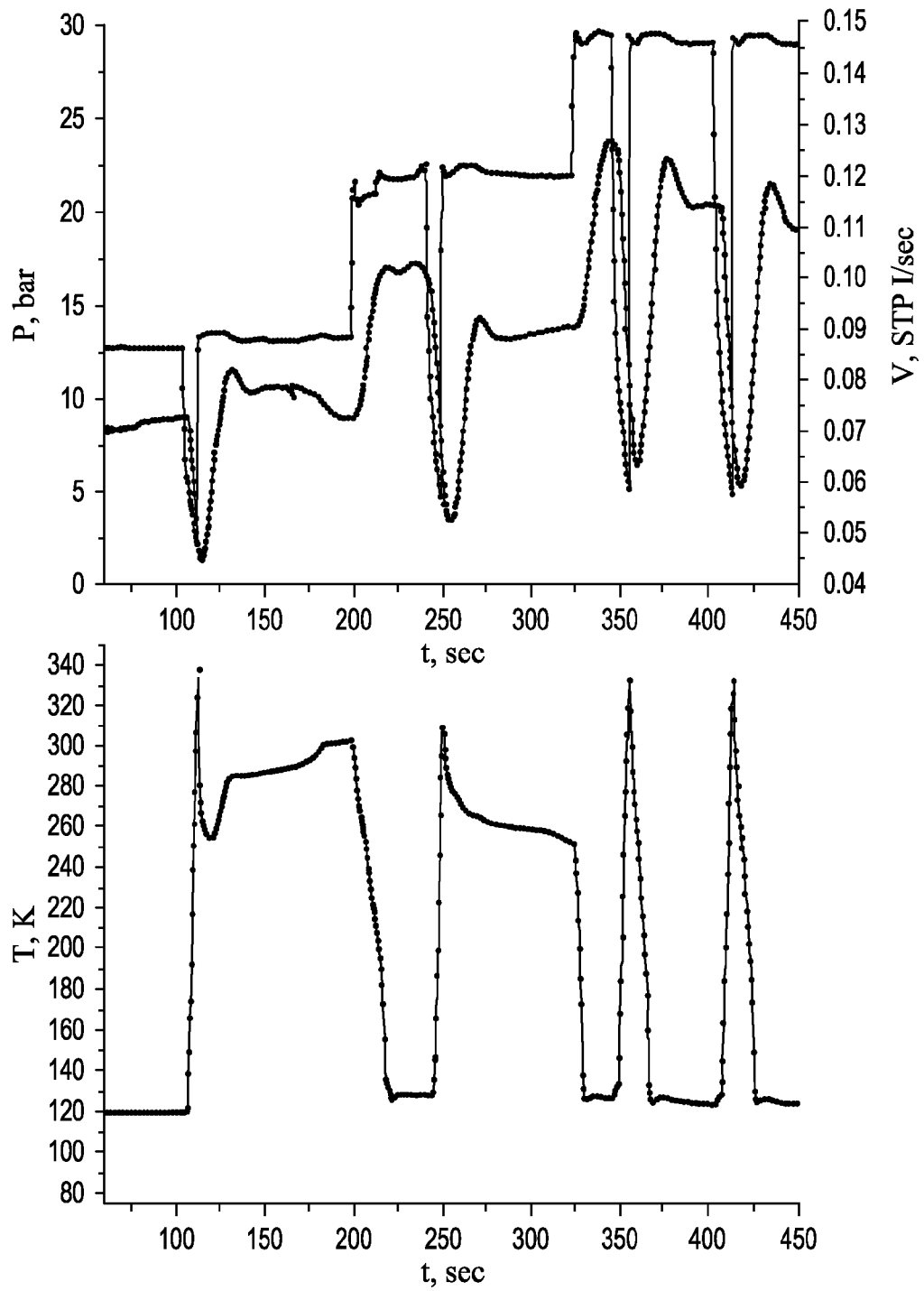
FIG. 1B provides an illustration of how to determine a minimum operating pressure for a cryogenic probe.

FIG. 1B displays how a minimum operating pressure P, and hence the minimum reduced pressure p, is determined experimentally. The upper curve in the top panel shows the pressure of nitrogen in the needle and the bottom curve in the top panel shows the resulting mass flow rate through the probe, displayed in units of standard liters per second through the needle. The bottom panel shows the needle tip temperature at the same times as the top plot. A heat load of 6.6 W was applied to the needle tip while these data were taken. For example, at an operating pressure of 12.6 bar and 22 bar a vapor-lock condition occurred at this level of heat load and flow rate, as evidenced by the failure of the needle tip temperature to recover its low temperature value when the flow was momentarily interrupted and then resumed. But at 28.5 bar of pressure, the tip temperature recovered its low temperature value reliably following a flow interruption. The downwards trend in the mass flow rate through the needle is indicative of being very close, yet slightly below the lowest acceptable pressure for reliable, continuous operation without vapor lock. These data suggest that about 29 bars of pressure is the lowest acceptable operating pressure in this illustrative embodiment. Thus, for this embodiment, in which a vacuum-jacketed needle with 22-cm long capillaries of 0.020-cm diameter for the inflow capillary and 0.030-cm diameter for the outflow capillary, under this heat load and flow rate, 29 bar is a typical minimum operating pressure. This corresponds to a minimum p=29 bar/33.9 bar=0.85. Hence, in this illustrative embodiment, "near critical" corresponds to a pressure no less than 85% of the critical pressure.

More generally, references herein to a "near-critical" pressure are intended to refer to a pressure that exceeds a minimum pressure determined to meet the conditions described above. In particular, once the minimum value of p has been determined, such as with the experimental procedure described, the "near-critical" pressure range includes all values of $p=P/P_c$ that are at or above the determined minimum pressure. While any supercritical pressure having p>1 is generally acceptable to avoid vapor lock, the inventors have discovered that in practice the minimum value of p that may be used without creating vapor-lock conditions may be lower, and use of such a lower value may advantageously improve system efficiency and simplicity.

Figure 1C:
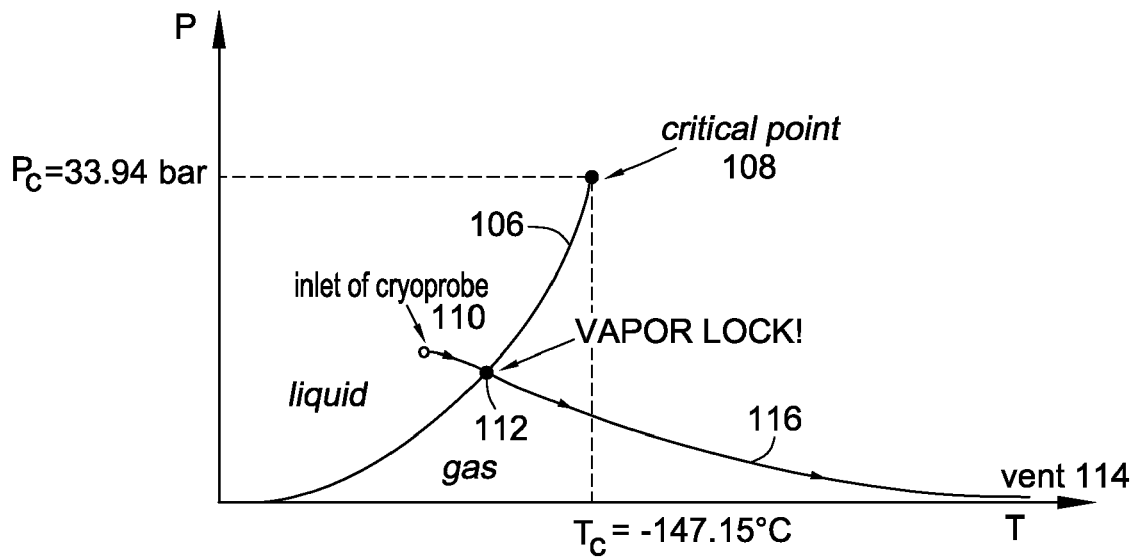
FIG. 1C uses a cryogen phase diagram to illustrate the occurrence of vapor lock with simple-flow cryogen cooling.

The occurrence of vapor lock in a simple-flow cryogen cooling system may be understood with reference to FIG. 1C, which for exemplary purposes shows the phase diagram for $N_2$, with liquid-gas phase line 106 terminating at critical point 108. The simple-flow cooling proceeds by compressing the liquid cryogen and forcing it to flow through a cryoprobe. Some pre-cooling may be used to force liquid-phase cryogen through an inlet 110 of the cryoprobe from the indicated point on the phase diagram to the region where the cryogen evaporates to provide evaporative cooling. The thermodynamic path 116 taken by the cryogen as it is forced from the inlet 110 to a vent 114 intersects the liquid-gas phase line 106 at point 112, where the evaporation occurs. Because the evaporation occurs at a point along the liquid-gas phase line 106 well below the critical point 108, there is a dramatic expansion of the volume of the flow stream as the much denser liquid evaporates into its gaseous phase, leading to the occurrence of vapor lock.

An alternative cryogen cooling technique that avoids vapor lock at the expense of a number of complexities exploits the Joule-Thomson effect. When a gas is compressed, there is a reduction in its enthalpy, the size of the reduction varying with the pressure. When the gas is then expanded through a small port (referred to as a "JT port" or "throttle") to a lower pressure, there is a reduction in temperature, with the resultant cooling being a function of the decrease in enthalpy during compression. With a heat exchanger provided between the compressor and expansion valve, progressively lower temperatures may be reached. In some instances, Joule-Thomson cooling uses cheaper gases like $CO_2$ or $N_2O$, although lower temperatures can be achieved with argon (Ar). There may be higher risks associated with Ar in addition to its higher cost, but both of these may be justified in some applications because of the rapid initiation and termination of freezing that may be provided.

Figure 1D:
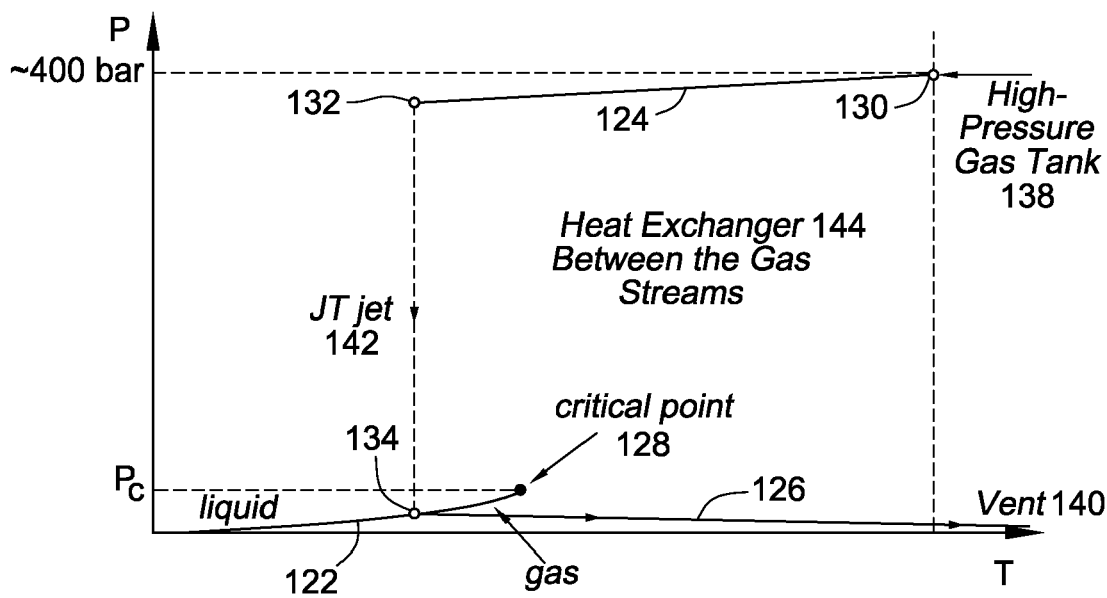
FIG. 1D uses a cryogen phase diagram to illustrate a cooling cycle used in Joule-Thomson cooling to avoid the occurrence of vapor lock.

Joule-Thomson cooling processes thus use a completely different cooling cycle than is used for simple-flow cryogen cooling, as illustrated with the phase diagram of FIG. 1D. The cooling cycle is shown superimposed on the $N_2$ phase diagram as a specific example, with the liquid-gas phase line 122 for $N_2$ terminating at its critical point 128. Nitrogen is initially provided at very high pressures at normal ambient (room) temperature at point 130 on the phase diagram. The pressure is typically about 400 bar, i.e. greater than ten times the pressure at the critical point 128. The $N_2$ flows within a cryoprobe along thermodynamic path 124 until it reaches the JT expansion port at point 132 on the phase diagram. The $N_2$ expands abruptly at the JT port, flowing in a JT jet 142 downwards in the phase diagram as its pressure decreases rapidly. The rapid expansion causes the $N_2$ downstream in the jet 142 to partially liquefy so that following the expansion at the JT jet 142, the liquefied $N_2$ is in thermal equilibrium with its gaseous phase. The nitrogen is thus at point 134 in the phase diagram, i.e. on the liquid-gas phase line 106 slightly above ambient pressure, and therefore well below the critical point 128. The nitrogen is heated on a return gas stream following thermodynamic path 126 where it may be used for cooling, and is subsequently exhausted to ambient conditions through a vent 140, perhaps on the way back to a controlling console. It is notable that Joule-Thomson cooling never approaches the critical point of the liquid-gas system, and that it uses predominantly evaporative-flow cooling.

The flow of the cooled gas in Joule-Thomson cooling is typically provided back along a side of the inlet high-pressure feed line. This counter-flow of the low-pressure return gas advantageously cools the incoming high-pressure gas before expansion. The effect of this heat exchanger 144 between the gas streams is evident in the phase diagram since the pressure along the inlet line to the JT port (thermodynamic path 124) falls due to its flow impedance as the stream of high-pressure gas is cooled by the counter-flow heat exchanger. Similarly, the pressure of the return stream (thermodynamic path 126) falls slightly as the cold, low-pressure nitrogen cools the incoming stream at high pressure through the counter-flow heat exchanger 144. The effects of the counter-flow heat exchanger 144 are beneficial in improving the efficiency the Joule-Thomson cooling, but limits to this efficiency result from trying to make the cryoprobe needle smaller in diameter. As the cryoprobe needle becomes smaller, the return-gas-flow velocity becomes larger, eventually reaching the speed of sound for typical volume flow rates and probe designs in probes having a diameter of about 1.5 mm. The Joule-Thomson cooling process continues to lose efficiency as the probe is miniaturized further, to the point where no more cooling power can be generated. Probes with diameters <1.2 mm are thereby severely limited by the physics of their operation to the point where they would have minimal cooling capacity, even if they could be reliably constructed at a reasonable cost. The cost of Joule-Thomson probe construction increases rapidly as the probe diameter is reduced, primarily because of the fabrication and assembly costs associated with the counter-flow heat exchanger.

Embodiments of the invention avoid the occurrence of vapor lock and permit decreased probe sizes by operating in cryogen pressure-temperature regimes that avoid any crossing of the liquid-gas phase line. In particular embodiments, cryogenic cooling is achieved by operating near the critical point for the cryogen. When operating in this region, heat flows into the near-critical cryogen from the surrounding environment since the critical-point temperature (e.g., −147° C. in the case of $N_2$) is much colder that the surrounding environment. This heat is removed by the flow of the near critical cryogen through the tip of a cryoprobe, even though there is no latent heat of evaporation to assist with the cooling process. While the scope of the invention is intended to include operation in any regime having a pressure greater than the critical-point pressure, the cooling efficiency tends to decrease as the pressure is increased above the critical pressure. This is a consequence of increasing energy requirements needed to achieve flow at higher operating pressures.

Figure 2A:
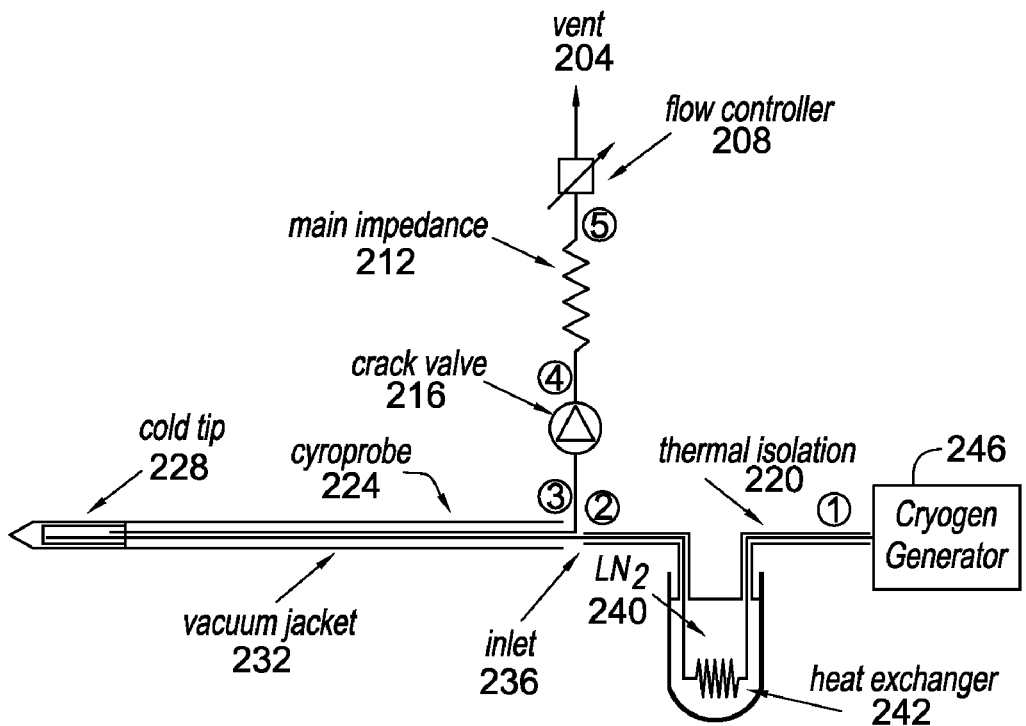
FIG. 2A is a schematic illustration of a cryogenic cooling system according to an embodiment of the invention.
Figure 2B:
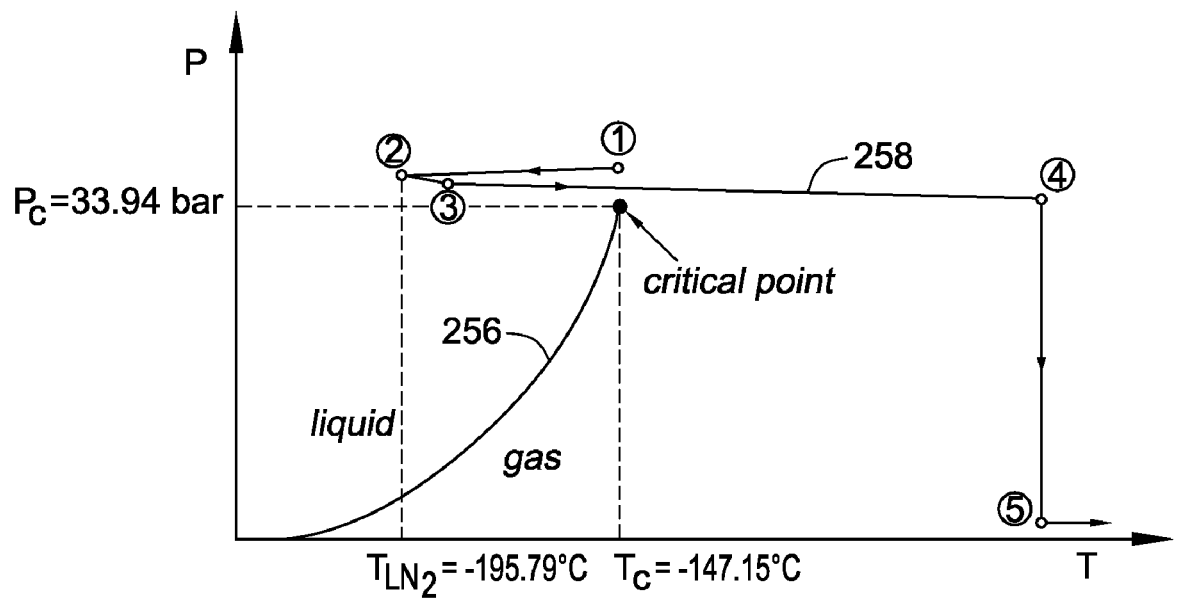
FIG. 2B uses a cryogen phase diagram to illustrate a method for cryogenic cooling in an embodiment of the invention.

FIG. 2A provides a schematic illustration of a structural arrangement for a cryogenic system in one embodiment, and FIG. 2B provides a phase diagram that illustrates a thermodynamic path taken by the cryogen when the system of FIG. 2A is operated. The circled numerical identifiers in the two figures correspond so that a physical position is indicated in FIG. 2A where operating points identified along the thermodynamic path are achieved. The following description thus sometimes makes simultaneous reference to both the structural drawing of FIG. 2A and to the phase diagram of FIG. 2B in describing physical and thermodynamic aspects of the cooling flow. For purposes of illustration, both FIGS. 2A and 2B make specific reference to a nitrogen cryogen, but this is not intended to be limiting. The invention may more generally be used with any suitable cryogen, as will be understood by those of skill in the art; merely by way of example, alternative cryogens that may be used include argon, helium, hydrogen, and oxygen. In FIG. 2B, the liquid-gas phase line is identified with reference label 256 and the thermodynamic path followed by the cryogen is identified with reference label 258.

A cryogenic generator 246 is used to supply the cryogen at a pressure that exceeds the critical-point pressure $P_c$ for the cryogen at its outlet, referenced in FIGS. 2A and 2B by label ○. The cooling cycle may generally begin at any point in the phase diagram having a pressure above or slightly below $P_c$, although it is advantageous for the pressure to be near the critical-point pressure $P_c$. The cooling efficiency of the process described herein is generally greater when the initial pressure is near the critical-point pressure $P_c$ so that at higher pressures there may be increased energy requirements to achieve the desired flow. Thus, embodiments may sometimes incorporate various higher upper boundary pressure but generally begin near the critical point, such as between 0.8 and 1.2 times $P_c$, and in one embodiment at about 0.85 times $P_c$. Different embodiments may have the initial cryogen pressure greater than about 0.8 times its critical-point pressure, but less than 5.0 times $P_c$, less than 2.0 times $P_c$, less than 1.5 times $P_c$, less than 1.2 times $P_c$, less than 1.1 times $P_c$, less than 1.01 times $P_c$, or less than 1.001 times $P_c$. Also, in several embodiments, it is advantageous for the initial temperature of the cryogen to be at or near the critical-point temperature $T_c$ so that in different embodiments the initial temperature is $T_c \pm 50°$ C., is $T_c \pm 25°$ C., is $T_c \pm 10°$ C., is $T_c \pm 5°$ C., is $T_c \pm 1°$ C., is $T_c \pm 0.1°$ C., or is substantially equal to $T_c$.

The cryogen is flowed through a tube, at least part of which is surrounded by a reservoir 240 of the cryogen in a liquid state, reducing its temperature without substantially changing its pressure. In FIG. 2A, reservoir is shown as liquid $N_2$, with a heat exchanger 242 provided within the reservoir 240 to extract heat from the flowing cryogen. Outside the reservoir 240, thermal insulation 220 may be provided around the tube to prevent unwanted warming of the cryogen as it is flowed from the cryogen generator 246. At point ○, after being cooled by being brought into thermal contact with the liquid cryogen, the cryogen has a lower temperature but is at substantially the initial pressure. In some instances, there may be a pressure change, as is indicated in FIG. 2B in the form of a slight pressure decrease, provided that the pressure does not drop substantially below the critical-point pressure $P_c$, i.e. does not drop below the determined minimum pressure. In the example shown in FIG. 2B, the temperature drop as a result of flowing through the liquid cryogen is about 47° C.

The cryogen is then provided to a device for use in cryogenic applications. In the exemplary embodiment shown in FIG. 2A, the cryogen is provided to an inlet 236 of a cryoprobe 224, such as may be used in medical cryogenic applications, but this is not a requirement. At the point when the cryogen is provided to such a device, indicated by label ○ in FIGS. 2A and 2B, there may be a slight change in pressure and/or temperature of the cryogen as it moves through an interface with the device, i.e. such as when it is provided from the tube to the cryoprobe inlet 236 in FIG. 2A. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Thermal insulation along the shaft of the cryotherapy needles, and along the support system that delivers near-critical freeze capability to these needles, may use a vacuum of better than one part per million of atmospheric pressure. Such a vacuum may not be achieved by conventional two-stage roughing pumps alone. The percutaneous cryotherapy system in an embodiment thus incorporates a simplified method of absorption pumping rather than using expensive and maintenance-intensive high-vacuum pumps, such as diffusion pumps or turbomolecular pumps. This may be done on an internal system reservoir of charcoal, as well as being built into each individual disposable probe.

Embodiments of the system incorporate a method of absorption pumping in which the liquid nitrogen bath that is used to sub-cool the stream of incoming nitrogen near its critical point is also used to cool a small volume of clean charcoal. The vast surface area of the charcoal permits it to absorb most residual gas atoms, thus lowering the ambient pressure within its volume to well below the vacuum that is used to thermally insulate the needle shaft and the associated support hardware. This volume that contains the cold charcoal is attached through small-diameter tubing to the space that insulates the near-critical cryogen flow to the needles. Depending upon the system design requirements for each clinical use, the charcoal may be incorporated into the cooling reservoir of liquid cryogen 240 seen in FIG. 2A, or become part of the cryoprobe 224, near the connection of the extension hose near the inlet 236. Attachments may be made through a thermal contraction bayonet mount to the vacuum space between the outer shaft of the vacuum-jacketed needles and the internal capillaries that carry the near-critical cryogen, and which is thermally insulated from the surrounding tissue. In this manner, the scalability of the system extends from simple design constructions, whereby the charcoal-vacuum concept may be incorporated into smaller reservoirs where it may be more convenient to draw the vacuum. Alternatively, it may be desirable for multiple-probe systems to individually incorporate small charcoal packages into each cryoprobe near the junction of the extension close/cryoprobe with the machine interface 236, such that each hose and cryoprobe draws its own vacuum, thereby further reducing construction costs.

Flow of the cryogen from the cryogen generator 246 through the cryoprobe 224 or other device is controlled in the illustrated embodiment with an assembly that includes a crack valve 216, a flow impedance, and a flow controller. The cryoprobe 224 itself may comprise a vacuum jacket 232 along its length and may have a cold tip 228 that is used for the cryogenic applications. Unlike a Joule-Thomson probe, where the pressure of the working cryogen changes significantly at the probe tip, these embodiments of the invention provide relatively little change in pressure throughout the probe. Thus, at point $\bigcirc$, the temperature of the cryogen has increased approximately to ambient temperature, but the pressure remains elevated. By maintaining the pressure above the critical-point pressure $P_c$ throughout the process, the liquid-gas phase line 256 is never encountered along the thermodynamic path 258 and vapor lock is thereby avoided. The cryogen pressure returns to ambient pressure at point $\bigcirc$ before passing through the flow controller 208, which is typically located well away from the cryoprobe 224. The cryogen may then be vented through vent 204 at substantially ambient conditions.

Figure 3:
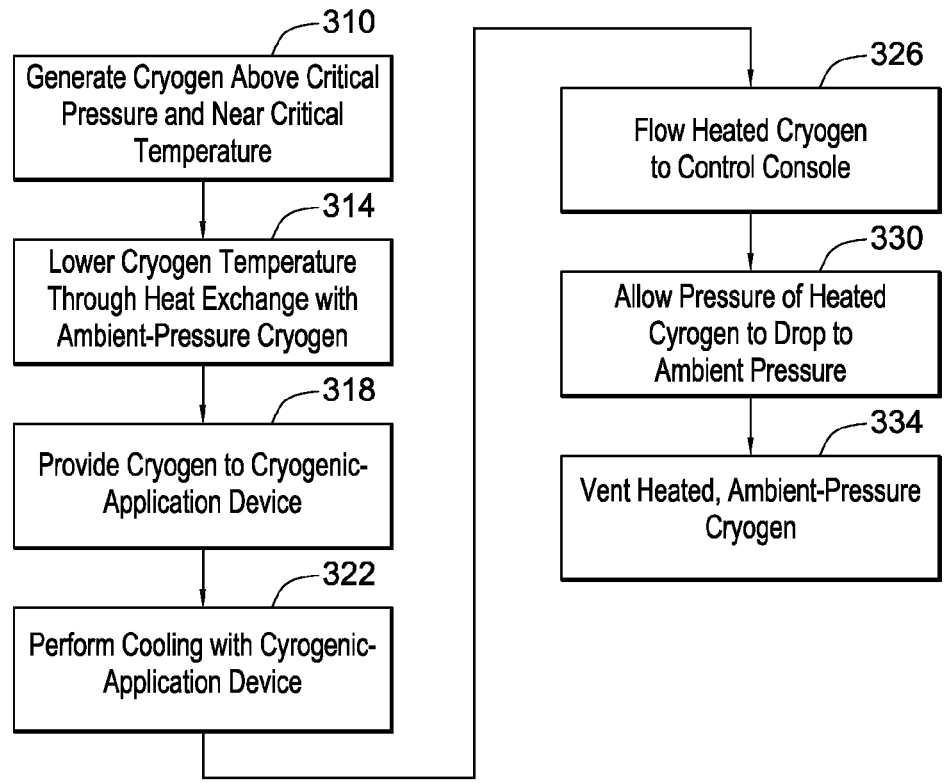
FIG. 3 provides a flow diagram that summarizes aspects of the cooling method of FIG. 2A.

A method for cooling in one embodiment in which the cryogen follows the thermodynamic path shown in FIG. 2B is illustrated with the flow diagram of FIG. 3. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For instance, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Figure 4:
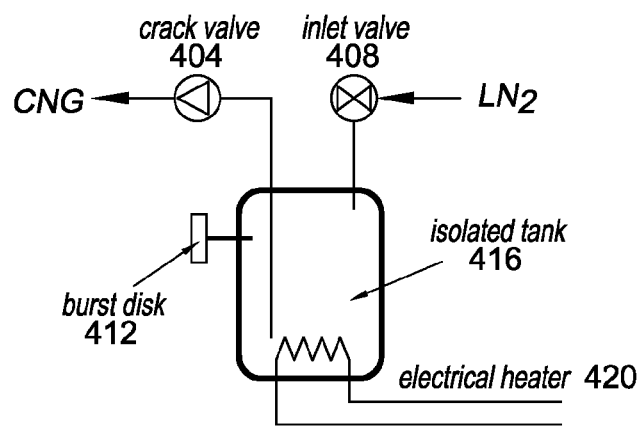
FIG. 4 is a schematic illustration of a cryogenic cooling system according to another embodiment of the invention.

There are a variety of different designs that may be used for the cryogen generator 246 in providing cryogen at a pressure that exceeds the critical-point pressure, or meets the near-critical flow criteria, to provide substantially uninterrupted cryogen flow at a pressure and temperature near its critical point. In describing examples of such designs, nitrogen is again discussed for purposes of illustration, it being understood that alternative cryogens may be used in various alternative embodiments. FIG. 4 provides a schematic illustration of a structure that may be used in one embodiment for the cryogen generator. A thermally insulated tank 416 has an inlet valve 408 that may be opened to fill the tank 416 with ambient liquid cryogen. A resistive heating element 420 is located within the tank 416, such as in a bottom section of the tank 416, and is used to heat the cryogen when the inlet valve is closed. Heat is applied until the desired operating point is achieved, i.e. at a pressure that exceeds the near-critical flow criteria. A crack valve 404 is attached to an outlet of the tank 416 and set to open at the desired pressure. In one embodiment that uses nitrogen as a cryogen, for instance, the crack valve 404 is set to open at a pressure of about 33.9 bar, about 1 bar greater than the critical-point pressure. Once the crack valve 404 opens, a flow of cryogen is supplied to the system as described in connection with FIGS. 2A and 2B above.

A burst disk 412 may also be provided consistent with safe engineering practices to accommodate the high cryogen pressures that may be generated. The extent of safety components may also depend in part on what cryogen is to be used since they have different critical points. In some instances, a greater number of burst disks and/or check valves may be installed to relieve pressures before they reach design limits of the tank 416 in the event that runaway processes develop.

During typical operation of the cryogen generator, an electronic feedback controller maintains current through the resistive heater 420 to a level sufficient to produce a desired flow rate of high-pressure cryogen into the system. The actual flow of the cryogen out of the system may be controlled by a mechanical flow controller 208 at the end of the flow path as indicated in connection with FIG. 2A. The amount of heat energy needed to reach the desired cryogen pressures is typically constant once the inlet valve 408 has been closed. The power dissipated in the resistive heater 420 may then be adjusted to keep positive control on the mechanical flow controller 208. In an alternative embodiment, the mechanical flow controller 208 is replaced with the heater controller for the cryogen generator. In such an embodiment, once the crack valve 404 opens and high-pressure cryogen is delivered to the rest of the system, the feedback controller continuously adjusts the current through the resistive heater to maintain a desired rate of flow of gaseous cryogen out of the system. The feedback controller may thus comprise a computational element to which the heater current supply and flow controller are interfaced.

Figure 5:
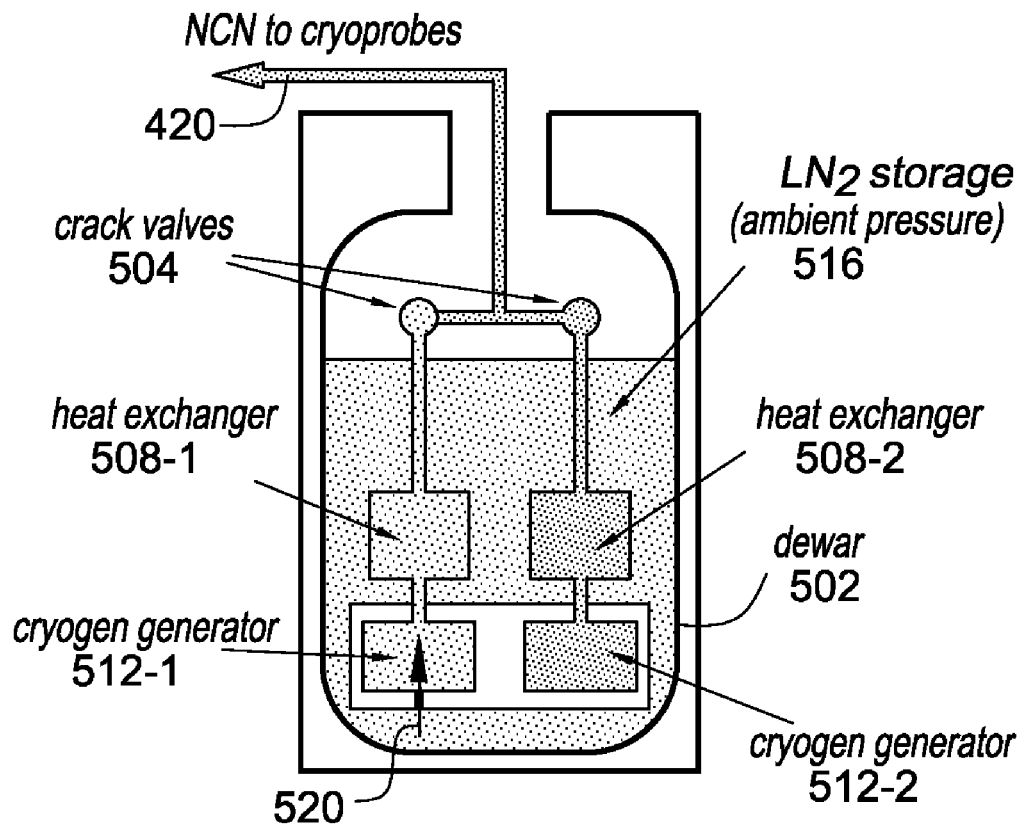
FIG. 5 is a schematic illustration of a cryogenic cooling system according to a further embodiment of the invention.

In another embodiment, a plurality of cryogen generators may be used to provide increased flow for specific applications. Such an embodiment is illustrated in FIG. 5 for an embodiment that uses two cryogen generators 512, although it is evident that a greater number may be used in still other embodiments. The plurality of cryogen generators 512 are mounted within an ambient-pressure cryogen Dewar 502 that contains a volume of ambient-pressure cryogen 516. Near-critical cryogen generated with the cryogen generators 512 is provided to a heat exchanger 508 that cools the cryogen in the same manner as described with respect to the heat exchanger 242 of FIG. 2A. A crack valve 504 associated with each of the cryogen generators 512 permits the high-pressure sub-cooled (i.e. cooled below the critical temperature) cryogen to be provided to cryogen-application devices along tube 420.

In a specific embodiment, each of the cryogen generators has a generally cylindrical shape with an internal diameter of about 30 cm and an internal height of about 1.5 cm to provide an internal volume of about one liter. The cryogen generators may conveniently be stacked, with each cryogen generator having its own independent insulating jacket and internal heater as described in connection with FIG. 4. A coil of tubing may be wrapped around the outer diameter of the stacked cryogen generators, with the output flow of high-pressure cryogen from each cryogen generator passing through a respective check valve before entering the inlet side of the coiled tubing heat exchanger. An outlet from the coil heat exchanger may advantageously be vacuum jacketed or otherwise insulated to avoid heating of the high-pressure cryogen as it flows towards the object being cooled. Such a stack of cryogen generators and the outer-coil heat exchanger may be mounted towards the bottom of a liquid-cryogen Dewar, such as a standard Dewar that holds about 40 liters of liquid $N_2$ when full. This Dewar may also be equipped with a convenient mechanism for filling the Dewar with liquid cryogen and for venting boil-off from the Dewar. In some instances, the liquid cryogen is maintained at or near ambient pressure, but may alternatively be provided at a different pressure. For instance, the liquid cryogen may be provided at a lower pressure to create a colder ambient liquid-cryogen bath temperature. In the case of liquid $N_2$, for example, the pressure may be dropped to about 98 torr to provide the cryogen at the liquid-$N_2$ slush temperature of about 63 K. While such an embodiment has the advantage of providing even lower temperatures, there may be additional engineering complexities in operating the liquid-cryogen Dewar below ambient pressure.

Operation of the multiple-cryogen-generator embodiments may advantageously be configured to provide a substantially continuous supply of high-pressure cryogen to the cryogenic device. The ambient liquid-cryogen 516 is used as a supply for a depleted cryogen generator 512, with the depleted cryogen generator 512 being refilled as another of the cryogen generators 512 is used to supply high-pressure or near-critical cryogen. Thus, the example in FIG. 5 with two cryogen generators is shown in an operational state where the first of the cryogen generators 512-1 has been depleted and is being refilled with ambient liquid cryogen 516 by opening its inlet valve to provide flow 520. At the same time, the second cryogen generator 512-2 has a volume of liquid cryogen that is being heated as described so that cryogen is being delivered as near-critical cryogen through its outlet crack valve 504. When the second cryogen generator 512-2 empties, the fill valve of the first cryogen generator 512-1 will be closed and its heater brought to full power to bring it to the point where it provides near-critical cryogen through its check valve. The inlet valve of the second cryogen generator 512-2 is opened so that it may engage in a refill process, the two cryogen generators 512 thereby having exchanged roles from what is depicted in FIG. 5.

The two cryogen generators 512 operate out of phase in this way until the entire Dewar 502 of ambient liquid cryogen is depleted, providing a substantially continuous flow of near-critical cryogen to the cryogenic application devices until that time. The system is thus advantageously scalable to meet almost any intended application. For example, for an application defined by a total cooling time and a rate at which cryogen is consumed by providing a Dewar of appropriate size to accommodate the application. As will be noted later, the cooling capacity of near-critical liquid $N_2$ allows efficient consumption of cryogen for maximal operation times and scaling of near-critical cryogen generators to total freeze time requirements dictated by specific application needs. For instance, the inventors have calculated that medical cryogenic freezing applications may use near-critical cryoprobes that consume about two liters of ambient liquid $N_2$ per instrument per hour.

Cryogen consumption for multiple-probe use provides one demonstration of the relative efficiency of near-critical liquid-$N_2$ systems compared to JT-base units with their large associated tanks, leading to much smaller functional size of the whole system configuration. Specifically, test data collected by the inventors suggests that a 1.6-mm near-critical liquid-$N_2$ 1.6-mm cryoprobe generates iceballs up to 4 cm in diameter within gelatin phantoms, similar to 2.4-mm JT-based current argon cryoprobes. Based on tests performed by the inventors, it is believed that 10 near-critical liquid-$N_2$ cryoprobes may produce a freeze volume comparable to no less than six JT-based argon cryoprobes. This allows a clear demonstration of appropriate system contents for currently accepted prostate use age of up to three cases per day. Current 2.4-mm cryoprobes utilize up to 40 PSI/min., thereby yielding no more than 80 minutes of total freeze time for a single probe from a single full argon tank (i.e. no more than 3200 PSI of usable pressure within a full 6000-PSI argon tank). Therefore, at least two of these argon tanks (160 minutes maximum) are generally used for each prostate case, which usually requires at least six 2.4-mm cryoprobes operating for two separate freeze cycles, the first usually 15 minutes and the second usually 10 minutes (i.e. $(6\times15)+(6\times10)=150$ probe-minutes total freeze time). In addition, one helium tank containing 2000 PSI is also used for each prostate case and the tank is of similar size and weight to the argon tanks. Combining the 80 kg (175 lbs), 0.38-$m^3$ Endocare system box (i.e. dimensions=$125\times48\times64$ $cm^3$) with the nine tanks (three for each case) weighing 182 kg each (1638 kg total) and displacing 0.062 $m^3$ each ($\pi\times12$ $cm^2\times137$ cm$\times9$=0.56 $m^3$ total) amounts to a total system weight of 1718 kp (i.e. 3780 lbs or 1.9 tons) within a 0.94-$m^3$ volume.

For the near-critical liquid-$N_2$ system, even ten cryoprobes used in parallel for 75 minutes (i.e. 25 minutes for each case) may thus be accommodated by a 25-liter Dewar (10 probes$\times$2 L/(probe hour)$\times$1.25 hours). Such a 25-liter Dewar may measure approximately 30 cm in diameter and 1.0 meter in height (i.e. 0.07 $m^3$ outer volume containing an insulated inner reservoir of 20-cm diameter and 0.75 meters in height, holding the 25-liter volume). This full Dewar may weight up to 40 kg (i.e. 20-kg Dewar weight+20 kg for 25 liters of liquid $N_2$ at 0.81 g/$cm^3$) and may be at least partially contained within the relatively empty Endocare box dimensions. A self-contained near-critical system provided by embodiments of the invention may thus weigh less than 120 kp (i.e. 80-kg box+the 40-kg full Dewar) and occupy a space of less than 0.40 $m^3$ (i.e. 03.7+0.07/2 $m^3$). Therefore, the following scaling chart provides a comparison of system performance in relation to practical clinical footprint within a surgical or radiological suite. For a handheld embodiment measuring approximately 25 cm in length, 50 cm in diameter, and containing 100 mL of liquid $N_2$ that can be run at variable rates for dermatological or limited interstitial freeze times:

| Type | Total Freeze Time (min) | Weight (kg) | Volume ($m^3$) | Case | Tanks |
|---|---|---|---|---|---|
| JT-Argon | 25 | 626 | 0.56 | 1 prostate | 2 Ar + 1 He |
| JT-Argon | 75 | 1718 | 0.94 | 3 prostate | 2 Ar + 1 He |
| NC-LN$_2$ | 75 | 120 | 0.40 | 3 prostate | none |
| NC-LN$_2$ | 5-20 | 1 | 0.0005 | 1 US-guided | single probe |

In summary, a near-critical liquid-nitrogen system may perform a full clinical day's caseload with less than half the clinical space requirement and an order of magnitude lower total weight that needs to be move around by technicians in setup, compared to current JT-based systems. Quantification of lower production costs is complicated by the existence of regional cost differences, but it is noted that currently costs for JT-based systems include an average un-reimbursable cost of about $200/case for compressed gases. The quantification of weight and space requirements also do not account for work time and safety impacts of hospital personnel having to move, connect, and secure high-pressure tanks.

Figure 6:
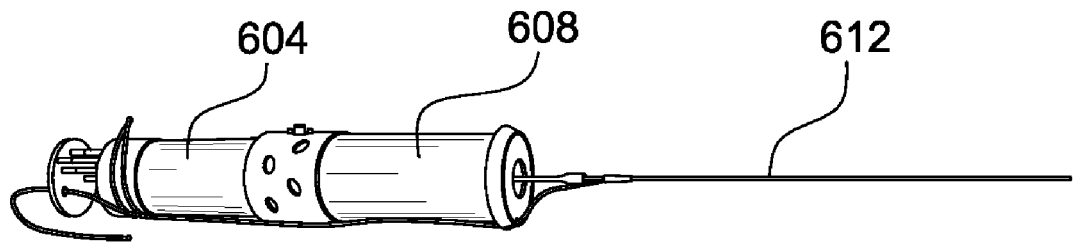
FIG. 6 is a photograph of an embodiment of a cryogenic system configured as a self-contained handheld device.

Some embodiments of the invention are especially suitable for low-volume short-duration cryogenic applications and are provided in the form of a self-contained handheld instrument, an example of which is shown with the photograph of FIG. 6. The integrated handheld instrument is especially suitable for use in applications involving a relatively brief cryogenic cooling, such as dermatology and interstitial low-volume freeze applications (e.g., treatment of breast fibroadenomas, development of cryo-immunotherapy). The structure of such an instrument is substantially as described in connection with FIG. 2A, with the components provided as a small self-contained unit. In particular, a relatively small cryogen generator 604 is connected in series with a small ambient liquid-cryogen tank 608, and a mounted cryogenic device 612. In the example shown in FIG. 6, the cryogenic device is a cryosurgical device that is permanently mounted to the instrument, although other types of cryogenic devices may be used in different embodiments. The self-contained handheld instrument may be provided as a disposable single-use instrument or may be rechargeable with liquid cryogen in different embodiments. The cryogen generator 604 and ambient liquid-cryogen tank 608 are vacuum jacketed or otherwise thermally insulated from their surrounding environment and from each other. For convenience of display, the instrument shown in FIG. 6 was photographed with an outer tube that holds the cryogen generator 604 and liquid-cryogen tank 608 under vacuum removed.

To be used, a switch is provided that allows an operator to control a small heater in the cryogen generator. The activation of the heater results in a flow of near-critical cryogen through set flow impedances that may be customized for a particular cooling task as described above. The flow of near-critical cryogen may continue until a reservoir of such cryogen within the instrument is expended, after which the instrument may be disposed of or recharged for future use. In some embodiments, such as for the cooling of sensitive receiver electronics, the handheld unit may interface with the object being cooled through a self-sealing interconnect port. This permits the object to be cooled to be disconnected from the disposable or rechargeable instrument between uses.

The handheld-instrument embodiments may be considered to be part of the continuum of scalability permitted by the invention. In particular, there is not only the option of providing sufficient near-critical or high-pressure cryogen for high-volume clinical or other uses, but also for short-duration low-volume uses. Over the full range of this continuum, operation is possible with very small cryogenic-device sizes, i.e. less than 1 mm, because there is no barrier presented by the phenomenon of vapor lock. For example, the ability to operate with small device sizes enables a realistic arrangement in which small rechargeable or disposable liquid-cryogen cartridges are provided as a supply, removing the need for large, inconvenient cryogenic systems. For instance, in the context of a medical application such as in a clinical setting for nerve ablation, or pain treatment, a small desktop Dewar of liquid $N_2$ may be used to provide liquid $N_2$ for refilling multiple cartridges as needed for nerve ablation. For a typical volume in such a clinical setting, the desktop Dewar would require recharging perhaps once a week to provide enough liquid for refilling the cartridges for use that week. Similar benefits may be realized with embodiments of the invention in industrial settings, such as where short-term cooling is provided by using disposable cartridges as needed. A minor accommodation for such applications would provide appropriate venting precautions for the tiny amount of boil-off that is likely to occur, even with well-insulated and/or pressurized cartridges. Embodiments of the invention thus enable an enhanced scope of cryogenic cooling options for numerous types of applications.

Figure 7A:
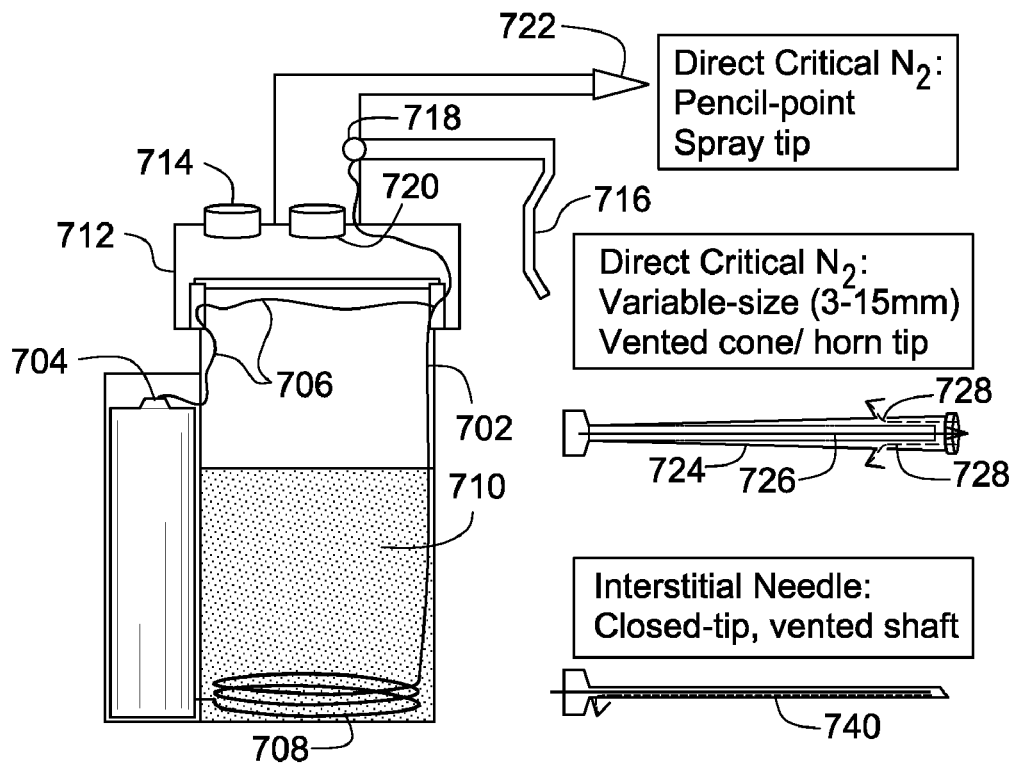
FIG. 7A shows another handheld embodiment that allows interchangeable tips to direct the near-critical nitrogen as a pinpoint spray or as a more evenly dispersed circular coverage for areas of various diameter.

A further embodiment uses the generation of near-critical cryogen for direct spraying for both medical (e.g., dermatology, and as an intraoperative surgical assist tool during any tumor resection) and non-medical applications. Current $LN_2$ dispensers for dermatology depend upon the spontaneous boiling of liquid $N_2$ through a pinhole nozzle, producing slow and relatively inaccurate dispensing of the cryogen, i.e. it effectively splatters out through the tiny hole. In addition, the inability to precisely control the freeze margins results in wider destruction of skin lesions with associated collateral damage of adjacent normal skin tissue. The sputtered delivery also makes liquid $N_2$ application close to crucial structures, such as small fatty deposits surround the eyes, more dangerous and generally avoided. FIG. 7A shows a battery-powered canister 702 with a small battery 704 placed along a back of the canister 702. The battery 704 drives the electric current along wires 706 to a coiled configuration 708 in the bottom of the canister. The canister may be filled with liquid nitrogen 710 and the lid 712 replaced. When the lid 712 makes a tight seal, a low power current flows to the coil 708 to generate critical-$N_2$ pressures (e.g., >600 PSI). The system is now in a charged state and ready for use, venting excess pressure (e.g. >700 PSI) through a calibrated valve 714. When a trigger 716 is pulled, a variable power control 718 activates increased electrical power to cause accelerated critical-$N_2$ production during spraying. Pulling the trigger 716 also activates the manual release of a special pressure valve 720 that is configured to close automatically if the pressure drops below 600 PSI. In this manner, only critical $N_2$ is released through the tip mechanism, avoiding vapor lock and/or sputtering. In order to achieve a precise but powerful spray, a pencil-point tip 722 may be provided to permit fine control by the physician.

Direct skin, or intraoperative, applications of critical $N_2$ may be further controlled by application of a vented cone tip 724. For example, this tip 724 may be provided as a disposable, single-use item (e.g. polyurethane) that gets quickly connected to the nozzle in place of the pencil-point tip 722. An open end of the cone may be provided in several variable sizes to accommodate a range from very small to larger lesions (e.g., 3, 5, 7, 9, 11, 13, 15, etc. mm). In operation, the cone tip is placed over a lesion, accommodating both exophytic (e.g. skintags), as well as flaw lesions (e.g. age spots). The critical $N_2$ travels down a central delivery tube, while the reflected spray gets vented out higher along sides of the cone. In this manner, only the skin/organ exposed beneath the cone tip containing the lesion gets treated and the vented gas stays away from the treatment site, further preserving collateral tissue.

Figure 7B:
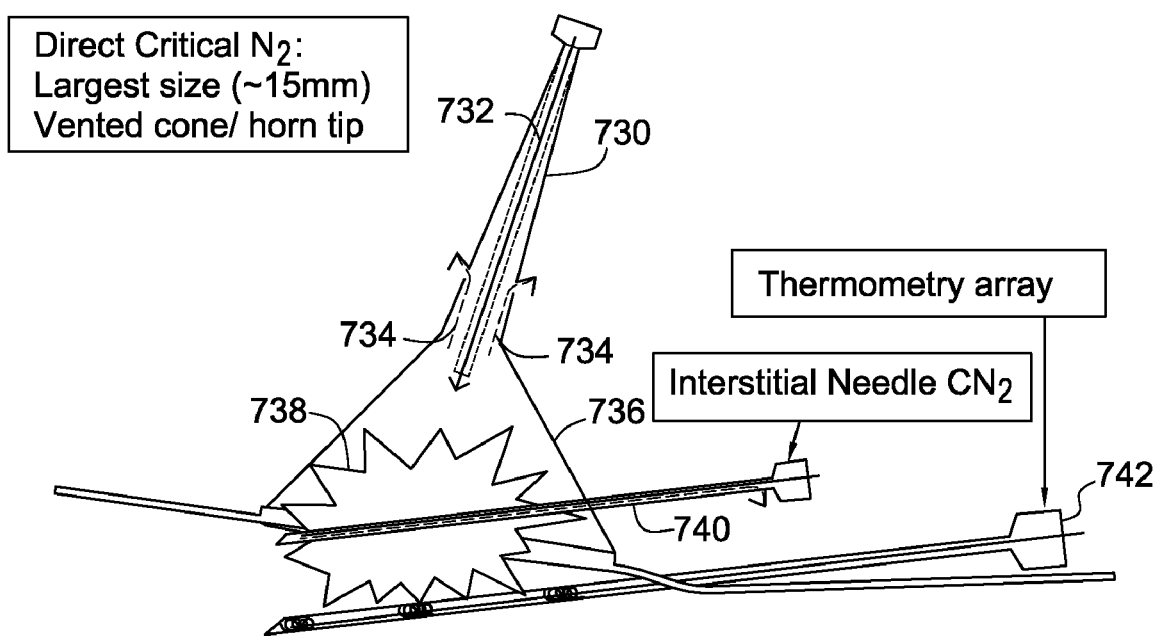
FIG. 7B illustrates a combined surface treatment of o tumor with a coned tip in combination with an interstitial vented needle, as well as deeper monitoring with a multi-point resistive thermometry array.

FIG. 7B illustrates that in still a further embodiment a vented needle 730 may be placed as the dispenser tip instead of pencil-point tip 722 or the vented cone 724. Such needles may be approximately 1 mm in outer diameter. Critical $N_2$ may travel down a central shaft 732 to a chamber 736 within the closed tip. For dermatological/intraoperative uses, the returning nitrogen 734 may be vented near the needle hub, or along an associated connecting tube. Such a needle may not require an insulated shaft since it may be directly placed into a skin, or intraoperative, tumor 738, potentially freezing along its entire exposed length.

Thermometry may also play a role in the treatment of skin, or intraoperative, tumors, helping to ensure thorough ablation of common malignant lesions. Basal cell carcinoma has been noted to require extremely low temperatures for complete necrosis, approaching −160° C. Therefore, a needle thermometry array may be placed directly beneath a tumor using either palpable or ultrasound guidance. Freezing may then safely progress until uniform thermometry readings of −160° C. are reached by either concentrated direct spray technique, interstitial needle placement, or their combination. Highly controlled tumor ablation of skin masses may also use a tabletop, multi-probe unit that allows computer control of the freezing process. For example, thermometry arrays 742 placed beneath the tumor would allow direct feedback to interstitial cryoneedles 740 placed within the tumor, shutting them off as soon as appropriate cytotoxic low temperatures are reached. The physician using a separately controlled, direct-spray technique may also directly treat more superficial aspects of the tumor.

Figure 8:
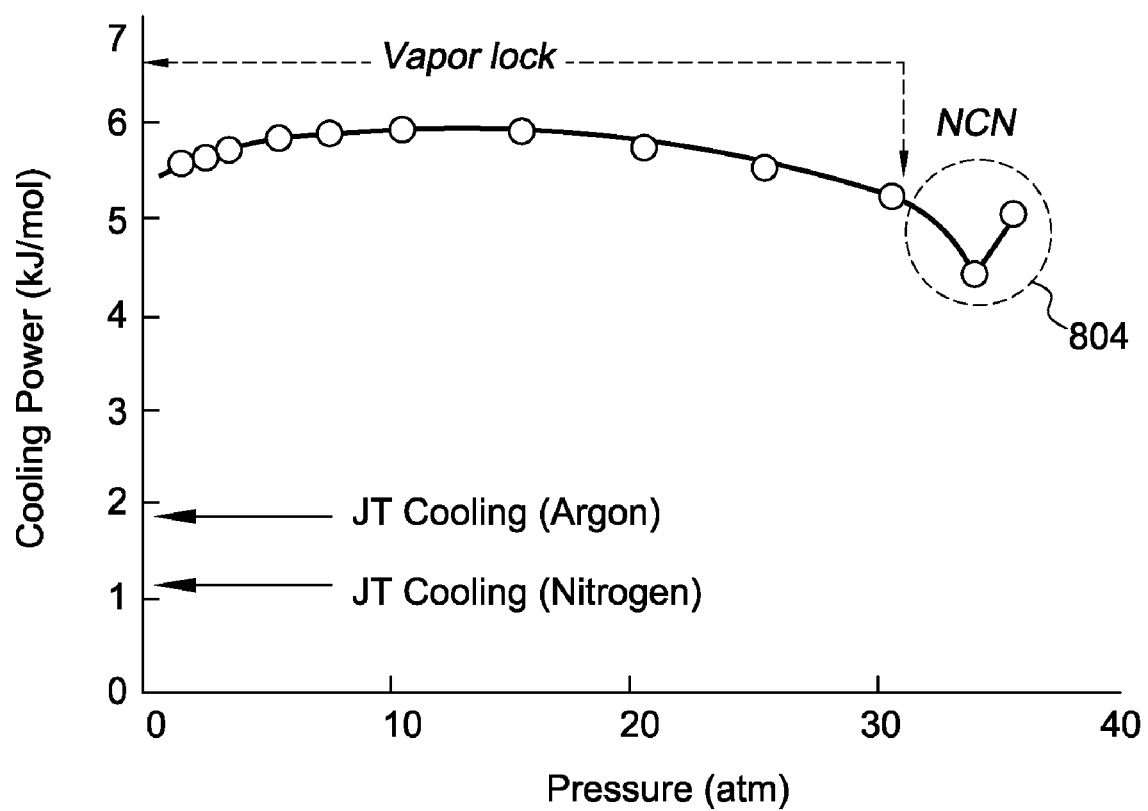
FIG. 8 provides a graphical comparison of cooling power for different cryogenic cooling processes.

Embodiments of the invention provide increased cooling power when compared with simple-flow cryogen cooling or with Joule-Thomson cooling, with one consequence being that the need for multiple high-pressure tanks of cryogen is avoided even without recycling processes. A comparison is made in FIG. 8 of the cooling power per mole of cryogen for the three different cooling systems. The top curve corresponds to the cooling cycle described herein in connection with FIG. 2B using $N_2$ as the cryogen, while the bottom two points identify the cooling power for Joule-Thomson processes that use argon and nitrogen as cryogens. The Joule-Thomson results represent maximum values for those processes because they were determined for perfect counter-flow heat exchange; this heat exchange becomes very inefficient as the probe diameter is reduced.

The presented results note that vapor lock of liquid $N_2$ may occur at lower pressures, but is avoided in the circled region 804 when the process meets the near-critical conditions for pressures near the critical-point pressure for $N_2$ of 33.94 bar. As previously noted, vapor lock may be avoided at near-critical flow conditions, although the efficiency of the process is improved when the pressure is near the critical-point pressure. The results illustrate that cooling cycles provided according to embodiments of the invention are more than five times as efficient as idealized Joule-Thomson cycles. Since the efficiency of embodiments that use pressures above the critical-point pressure is not substantially affected by changes in probe size, the cooling power per gram is often more than ten times greater than the cooling power for Joule-Thomson cycles. This greater efficiency is manifested by the use of substantially less, i.e. 1/5th-1/10th, of the exhaust gas flow, making the process much quieter, less disruptive, and without the need for bulky multiple-tank replacements.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method for cooling the surface of a cryoprobe using a cryogen having a critical point defined by a critical-point pressure and a critical-point temperature, the method comprising:

raising a pressure of cryogen above its critical-point pressure, said cryogen comprising $N_2$; and thereafter, placing the cryogen in thermal communication with the surface of a cryoprobe to increase a temperature of the cryogen along a thermodynamic path that maintains the pressure greater than the critical-point pressure for the duration that the cryogen and said surface are in thermal communication.

2. The method recited in claim 1 wherein the thermodynamic path increases the temperature of the cryogen to an ambient temperature.

3. The method recited in claim 2 further comprising reducing the pressure of the cryogen to an ambient pressure after removing the cryogen from thermal communication with said surface.

4. The method recited in claim 1 further comprising, after raising the pressure of the cryogen above its critical-point pressure and prior to placing the cryogen in thermal communication with said surface, reducing the temperature of the cryogen without decreasing the pressure of the cryogen below its critical-point pressure.

5. The method recited in claim 4 wherein reducing the temperature of the cryogen comprises placing the cryogen in thermal communication with a second liquid cryogen having a temperature lower than the temperature of the cryogen.

6. The method recited in claim 5 wherein the cryogen and second cryogen are chemically identical.

7. The method recited in claim 5 wherein the second liquid cryogen is substantially at ambient pressure.

8. The method recited in claim 1 wherein raising the pressure of the cryogen above its critical-point pressure comprises:

placing the cryogen within a thermally insulated tank; and applying heat within the thermally insulated tank at least until a predetermined pressure within the thermally insulated tank is reached.

9. A system for cooling the surface of a cryoprobe using a cryogen having a critical point defined by a critical-point pressure and a critical-point temperature, the system comprising:

means for raising a pressure of cryogen above a pressure value determined to provide the cryogen at a reduced molar volume that prevents vapor lock, said cryogen comprising $N_2$; and means for thereafter placing the cryogen in thermal communication with the surface of a cryoprobe to increase a temperature of the cryogen along a thermodynamic path that maintains a pressure greater than determined pressure value for the duration that the cryogen and said surface are in thermal communication.

10. The system recited in claim 9 further comprising means for reducing the pressure of the cryogen to an ambient pressure after removing the cryogen from thermal communication with said surface.

11. The system recited in claim 9 further comprising means for reducing the temperature of the cryogen without decreasing the pressure of the cryogen below its critical-point pressure after raising the pressure of the cryogen above its critical-point temperature and prior to placing the cryogen in thermal contact with said surface.

12. The system recited in claim 11 wherein the means for reducing the temperature of the cryogen comprises means for placing the cryogen in thermal communication with a second liquid cryogen having a temperature lower than the temperature of the cryogen.

13. The system recited in claim 9 wherein the means for raising the pressure of the cryogen comprises means for applying heat to the cryogen within a thermally insulated holding means until a predetermined pressure within the thermally insulated holding means is reached.

* * * * *